United States Patent [19]

Ladisch

[11] Patent Number: 4,551,449
[45] Date of Patent: Nov. 5, 1985

[54] AVOIDANCE OF THE IMMUNOSUPPRESSIVE AND ANTIPROLIFERATIVE EFFECTS OF LIPID EMULSIONS

[75] Inventor: Stephan Ladisch, Pacific Palisades, Calif.

[73] Assignee: The Regents of the University of California, Berkeley, Calif.

[21] Appl. No.: 552,489

[22] Filed: Nov. 16, 1983

[51] Int. Cl.$^4$ ............................................. A61K 31/56
[52] U.S. Cl. .................................................... 514/182
[58] Field of Search .................... 260/397.2; 424/238, 424/243; 514/182

[56] References Cited

U.S. PATENT DOCUMENTS 4,280,996  7/1981  Okamoto et al. .................... 424/238
4,340,594  7/1982  Mizushima et al. ................. 424/243

Primary Examiner—Elbert L. Roberts
Attorney, Agent, or Firm—Joseph E. Mueth

[57] ABSTRACT

Lipid emulsions for human therapy containing cholesterol or other sterols in an amount effective to substantially mitigate immunosuppressive and antiproliferative effects.

The use of these novel lipid emulsions in subjects receiving hyperalimentation therapy.

11 Claims, No Drawings

AVOIDANCE OF THE IMMUNOSUPPRESSIVE AND ANTIPROLIFERATIVE EFFECTS OF LIPID EMULSIONS

BACKGROUND OF THE INVENTION

Lipid emulsions are widely used in the treatment of patients who are not able to obtain adequate nutrition from their oral intake. These emulsions consist of (1) an oil, comprised of triglycerides, the primary nutritional component of the emulsion, (2) phospholipid as the emulsifying agent, and (3) glycerol to render the emulsion isotonic to the blood into which the emulsion is infused. Substantial benefits in the nutrition of these patients have resulted from the availability of lipid emulsions, through their provision of essential fatty acids and calories contained mainly in the oil.

The need for an emulsifying agent in these clinically used lipid emulsions results from the fact that the oil (e.g., soybean, safflower) cannot be dissolved or suspended in the aqueous solution required for intravenous infusion. The use of lecithin, a phospholipid, to form a stable emulsion of the oil comes from the knowledge that when phospholipids are sonicated in aqueous solutions, they become micelles which remain in suspension and also can hold an oil in suspension. Other natural compounds, such as cholesterol, have also been used, in combination with phospholipids such as lecithin, in laboratory studies to form micelles, but cholesterol or other sterols have never been used as emulsifying agents in lipid emulsions for human i.v. infusion.

Separately from inhibitory effects on cellular functions of the lipid emulsion which are used in clinical practice (discussed in the next paragraph), micelles of lecithin and/or cholesterol have been the subject of laboratory studies directed toward understanding the exchange of cell membrane lipids with their extracellular environment. These studies have demonstrated that the lipid composition of the extracellular environment can alter the lipid composition of the cell membrane and modulate certain cellular processes including cell proliferation. Exposure of cells to lecithin micelles may interfere with certain cellular functions. Whether micelles composed of a combination of lecithin and cholesterol have less inhibitory effects has not yet been resolved in the published literature; some studies have shown less, and some studies equal, inhibition by micelles composed of lecithin and cholesterol versus lecithin alone. No studies of these lipids in combination with the oil used in lipid emulsions have been published.

The problem addressed by this invention is the fact that in recent years significant adverse effects of lipid emulsions have been reported. Several medical journals have recommended great restriction in the use of lipid emulsions such as Intralipid ® because of these side effects, Editorial "Parenteral nutrition in the newborn—a time for caution" *Lancet* ii: 838–839, 1980, which include, among others, suppressive effects on immune responses. These immunosuppressive effects include diminished bacterial defenses, G. W. Fischer et al., *Lancet* ii: 819–820, 1980, depressed reticuloendothelial system function, Z. Friedman et al, *Pediatrics* 61: 694–698, 1978, and inhibition of the lymphoproliferative responses which are a component of cell-mediated immune responses, S. Ladisch et al, *Clin. Immunol. Immunopath.* 25: 196–202, 1982. The cause of these immunosuppressive effects has not been identified.

These examples of detrimental clinically important side effects of lipid emulsions, and the recommendations of restrictions on the clinical use of the emulsions, clearly define a problem with the lipid emulsions and suggest that it is of great urgency that steps should be taken to avoid these adverse side effects. However, despite wide awareness of the serious side effects of the lipid emulsions as currently formulated, no solution to the problem has been found. It is this serious problem which is addressed by the present invention, which proposes that, by modification of the composition of the lipid emulsions, the immunosuppressive effects of these emulsions will be abrogated.

Specific background for understanding my invention claimed herein is derived from my studies on the mechanism by which lipid emulsions suppress one of the component steps of cell mediated immune responses, the proliferation of normal lymphocytes in response to stimulation by an antigen (such as a bacterial antigen). This proliferative phase of the cellular immune response is the normal division of lymphocytes (present in the blood), when they are exposed to such foreign antigens. Adequate division of the cells is necessary to ultimately result in an adequate immunologic response which will counteract an infectious process or eliminate foreign cells. Therefore, any agent which is immunosuppressive may interfere with the resolution of infections, the rejection of foreign cells, and possibly the rejection of tumor cells. My studies of the mechanism of the immunosuppressive effect of lipid emulsions have shown that the T lymphocyte is prevented from proliferating, and thereby is adversely affected, by the lipid emulsion. I have also found that such lipid emulsions cause inhibition of proliferation of essentially all other types of cells tested. In studying the mechanism of the inhibition of cell proliferation by lipid emulsions, using tumor cells for these studies, I found that this agent affects the post-DNA synthetic phase of cell division. This phase, known as the $G_2$ phase, represents the period of time during which the cell increases its volume and total amount of membrane, to be able to divide into two daughter cells.

The present invention relates to the modification of the formulation of lipid emulsions such as Intralipid ® and Liposyn ® to abrogate the immunosuppressive effects which have been observed. As previously stated, the known lipid emulsions consist of three components: triglyceride, glycerol, and lecithin. In the absence of decomposition of the lipids contained in the lipid emulsions, I have found that the lecithin in the lipid emulsions accounts for the inhibitory effect, in the following fashion:

Lecithin and cholesterol exist in the cell membrane in equimolar amounts. Also, certain lipids, especially cholesterol, exchange freely between cells and their environment. I therefore hypothesized that because the commercially available, clinically used, lipid emulsions contain essentially no cholesterol, these lipid emulsions withdraw cholesterol from the membranes of cells exposed to the lipid emulsion by a process of passive exchange. Passive exchange acts to equalize the ratio of cholesterol to lecithin in the lipid emulsion (infinitely low) with that of the cell membranes (approximately 1:1 molar). Using radiolabelled lecithin and cholesterol, I have proved the correctness of this hypothesis by showing that cells in the presence of one of the lipid emulsions, Intralipid ®, lose cholesterol from their membranes. The significance of this finding is that adequate membrane cholesterol content is necessary for the cell to progress through the G₂ phase of the cell cycle and to divide. My findings therefore provided an explanation for the inhibitory effects of the clinically used lipid emulsions. That is, these lecithin-containing, cholesterol-free emulsions of vegetable oils withdraw cholesterol from the cell membrane. By depleting the membrane cholesterol content the lipid emulsions thereby inhibit cell division, arresting the proliferative process in the $G_2$ phase of the cell cycle.

The present invention is based on my ultimate finding that, to my surprise, by changing the composition of lipid emulsions only by adding a small amount of cholesterol to the triglyceride and lecithin comprising the known lipid emulsions, the immunosuppressive effects of the emulsions are abrogated, by preventing depletion of cell membrane cholesterol content by the lipid emulsion.

SUMMARY OF THE INVENTION

Briefly, the present invention comprises lipid emulsions for human therapy containing cholesterol or other sterols in an amount effective to substantially mitigate immunosuppressive and antiproliferative effects.

The invention also includes the administration of novel lipid emulsions for human therapy containing cholesterol or other sterols in an amount effective to substantially mitigate immunosuppressive and antiproliferative effects to subjects receiving hyperalimentation.

It is an object of this invention to provide a novel lipid emulsion for human therapy.

It is a further object of this invention to provide a novel lipid emulsion which eliminates the immunosuppressive and antiproliferative effects.

Still further, it is an object of this invention to treat patients with a novel lipid emulsion.

These and other objects and advantages of the invention will be apparent from the detailed description which follows.

My studies of the molecular mechanism of inhibition of cell proliferation by Intralipid ® reveal that the lecithin component of the emulsion is the predominant one responsible for the antiproliferative effects. According to the preferred embodiment of this invention the composition of lipid emulsions is modified to include equimolar concentrations of lecithin and cholesterol to abrogate the anti-proliferative effects.

DESCRIPTION OF THE PREFERRED EMBODIMENTS

The preferred formulation modifications would be those, according to this invention, which would bring the cholesterol/lecithin ratio of the lipid emulsion closer to the biologically normal value of close to 1.0 on a molar basis. To reiterate, then, the concept of this application is to normalize the cholesterol/lecithin ratio of lipid emulsion particles.

It is to be understood that the cholesterol can be obtained from a variety of sources including naturally occurring sources such as egg yolk which simultaneously provides the lecithin. Cholesterol per se is quite acceptable, however, this invention is applicable to all cholesterol-like compounds, viz, sterols. Lecithin can be replaced by other phospholipids. The preferred ratio of 1:1 can also be varied considerably.

Below is an initial list of potential approaches which could be used to modify the formula of lipid emulsions to achieve the above result within this invention.

(1) Add to the lipid emulsion a quantity of pure cholesterol equimolar to the quantity of phospholipid present in the lipid emulsion.

(2) Instead of adding a quantity of cholesterol equimolar to that of the phospholipid presently used in preparing lipid emulsions, formulate the lipid emulsion with smaller amounts of cholesterol in combination with smaller equimolar amounts of lecithin.

(3) Substitution of egg yolk lipids for an artificial combination of lecithin and cholesterol. The phospholipid currently used in some lipid emulsions is extracted from egg yolk. Egg yolk also contains cholesterol. Egg yolk contains (per gram solids) 0.66 gm lipids, including 0.14 gm lecithin, 0.03 gm cholesterol, and the remainder consisting mainly of unsaturated and saturated fatty acids as triglycerides. Thus, egg yolk might be used to obtain both the lecithin and cholesterol necessary to form a stable emulsion, and therefore the use of egg yolk as a single source for the emulsifying lipids (cholesterol and lecithin) is envisioned by this invention.

(4) Substitution of total egg yolk lipids for all the lipids present in the emulsion. Because in addition to containing cholesterol and phospholipid (lecithin), egg yolk also contains triglycerides composed of essential and nonessential fatty acids, the use of egg yolk lipids as a single source for all the lipids comprising the lipid emulsion is also envisioned by this invention.

This Example is presented solely to illustrate the invention. In the Example, the parts and percentages are by weight.

EXAMPLE

A clinically used lipid emulsion is composed of 20% triglyceride, 1.25% egg yolk lecithin, 2.5% glycerol, and the balance water. To this lipid emulsion is added an amount of cholesterol in an amount which is equimolar with respect to the lecithin. The resulting modified lipid emulsion is administered by intravenous infusion to patients on hyperalimintation to mitigate immunosuppressive and antiproliferative effects of the lipid emulsion.

The foregoing Example is equally applicable to lipid emulsions containing 10% tiglyceride.

The Example is also applicable to Intralipid ® and Liposyn ® commercially available lipid emulsions.

Having fully described the invention it is intended that it be limited only by the lawful scope of the appended claims.

I claim:

1. The method which comprises the administration to humans on hyperalimentation of a lipid emulsion which contains a sterol, said sterol being present in an amount effective to substantially mitigate immunosuppressive and antiproliferative effects caused by conventional lipid emulsions in humans on hyperalimentation.

2. The method of claim 1 wherein said sterol is cholesterol.

3. The method of claim 1 wherein the said emulsion includes triglyceride, a phospholipid, and glycerol.

4. The method of claim 3 wherein the phospholipid is lecithin.

5. The method of claim 2 wherein the triglyceride is 10% to 20% by weight, a phospholipid 1.25%, the glycerol 2.5% and the balance water and to which cholesterol is added to make the lecithin-cholesterol ratio equimolar.

6. The method of claim 1 to humans receiving hyperalimentation.

7. The method of claim 1 wherein the natural product is egg yolk.

8. The method of claim 1 wherein the natural product contains cholesterol and phospholipid.

9. The method of claim 1 wherein the said lipid emulsion is entirely prepared from a cholesterol-containing natural product.

10. The method of claim 9 wherein the natural product is egg yolk.

11. The method of claim 9 wherein the natural product contains cholesterol and phospholipid.

* * * * *